United States Patent [19]
Sano et al.

[11] Patent Number: 5,661,012
[45] Date of Patent: Aug. 26, 1997

[54] METHOD FOR THE PRODUCTION OF L-THREONINE BY FERMENTATION, USING MUTATED DNA ENCODING ASPARTOKINASE III

[75] Inventors: Konosuke Sano; Hiroyuki Kojima; Yuri Ogawa, all of Kawasaki, Japan

[73] Assignee: Ajinomoto Co., Inc., Tokyo, Japan

[21] Appl. No.: 256,136

[22] PCT Filed: Nov. 10, 1993

[86] PCT No.: PCT/JP93/01640

§ 371 Date: Jul. 1, 1994

§ 102(e) Date: Jul. 1, 1994

[87] PCT Pub. No.: WO94/11517

PCT Pub. Date: May 26, 1994

[30] Foreign Application Priority Data

Nov. 10, 1992 [JP] Japan .................................. 4-300021

[51] Int. Cl.$^6$ .............................. C12N 9/12; C12N 15/54; C12P 13/08
[52] U.S. Cl. .................... 435/115; 435/194; 435/252.33; 536/23.2
[58] Field of Search ............................... 435/194, 252.3, 435/252.33, 115; 536/23.2

[56] References Cited

FOREIGN PATENT DOCUMENTS

| | | |
|---|---|---|
| 55-131397 | 10/1980 | Japan . |
| 56-15696 | 2/1981 | Japan . |
| 59-31691 | 2/1984 | Japan . |
| 3 501682 | 4/1991 | Japan . |
| WO93/19190 | 9/1993 | WIPO . |

OTHER PUBLICATIONS

Cassan et al., *J. Biol. Chem.*, 261(3):1052–1057, Jan. 25, 1986.
Mizukami et al., *Agric. Biol. Chem.* 50(4):1015–1018 1986.

*Primary Examiner*—Keith D. Hendricks
*Attorney, Agent, or Firm*—Oblon, Spivak, McClelland, Maier & Neustadt, P.C.

[57] ABSTRACT

A DNA containing a gene which codes for aspartokinase III originating in Escherichia bacteria and which has in the coding region a mutation which releases the feedback inhibition by lysine on the aspartokinase III, a recombinant DNA wherein the DNA is linked to a vector DNA capable of autonomous replication in Escherichia bacteria, a microorganism belonging to the genus Escherichia which has been transformed by the introduction of the above mentioned recombinant DNA into the cells thereof, and a method for the production of L-threonine which comprises culturing the microorganism in a fermentation medium, producing and accumulating L-threonine in the culture medium, and collecting the L-threonine from said-culture medium. Escherichia bacteria-derived AK III genes are obtained which sufficiently release the feedback inhibition due to lysine. Introduction of these genes into threonine-producing bacteria results in new threonine-producing bacteria which are much improved in their threonine production over those of the prior art. Use of these threonine-producing bacteria provides a much more excellent method for the production of L-threonine by fermentation than the conventional methods.

8 Claims, 7 Drawing Sheets

```
AAT CCG CCG CTG TTC CGC GCT CTG GCG CTT CGT CGC AAT CAG ACT CTG                    1513
Asn Pro Pro Leu Phe Arg Ala Leu Ala Leu Arg Arg Asn Gln Thr Leu
                300                                         310
                                            A →       A →   T →
CTC ACT TTG CAC AGC CTG AAT ATG CTG CAT TCT CGC GGT TTC CTC GCG                    1561
Leu Thr Leu His Ser Leu Asn Met Leu His Ser Arg Gly Phe Leu Ala
                                    320           (A)
                        → Ile                         → Asp   → Phe
        T →     A →
GAA GTT TTC GGC ATC CTC GCG CGG CAT AAT ATT TCG GTA GAC TTA ATC                    1609
Glu Val Phe Gly Ile Leu Ala Arg His Asn Ile Ser Val Asp Leu Ile
        330                                                 340
→ Leu           → Met       → Met
                                        T →
ACC ACG TCA GAA GTG AGC GTG GCA TTA ACC CTT GAT ACC ACC GGT TCA                    1657
Thr Thr Ser Glu Val Ser Val Ala Leu Thr Leu Asp Thr Thr Gly Ser
                                350         (B)
                        → Met                  → Ile

ACC TCC ACT GGC GAT ACG TTG CTG ACG CAA TCT CTG CTG ATG GAG CTT                    1750
Thr Ser Thr Gly Asp Thr Leu Leu Thr Gln Ser Leu Leu Met Glu Leu
            360                                         370
```

FIG. 7

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2147 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: -35_signal
        ( B ) LOCATION: 242..249

( i x ) FEATURE:
        ( A ) NAME/KEY: -10_signal
        ( B ) LOCATION: 265..273

( i x ) FEATURE:
        ( A ) NAME/KEY: primer_bind
        ( B ) LOCATION: 536..555

( i x ) FEATURE:
        ( A ) NAME/KEY: primer_bind
        ( B ) LOCATION: 2128..2147

( i x ) FEATURE:
        ( A ) NAME/KEY: RBS
        ( B ) LOCATION: 575..578

( i x ) FEATURE:
        ( A ) NAME/KEY: mat_peptide
        ( B ) LOCATION: 584..1930

( i x ) FEATURE:
        ( A ) NAME/KEY: terminator
        ( B ) LOCATION: 1941..1968

( i x ) FEATURE:
        ( A ) NAME/KEY: CDS
        ( B ) LOCATION: 584..1930

( x i ) SEQUENCE DESCRIPTION: SEQ ID NO:1:

```
TCGAAGTGTT  TCTGTAGTGC  CTGCCAGGCA  GCGGTCTGCG  TTGGATTGAT  GTTTTTCATT          60

AGCAATACTC  TTCTGATTTT  GAGAATTGTG  ACTTTGGAAG  ATTGTAGCGC  CAGTCACAGA         120

AAAATGTGAT  GGTTTTAGTG  CCGTTAGCGT  AATGTTGAGT  GTAAACCCTT  AGCGCAGTGA         180

AGCATTTATT  AGCTGAACTA  CTGACCGCCA  GGAGTGGATG  AAAAATCCGC  ATGACCCCAT         240

CGTTGACAAC  CGCCCCGCTC  ACCCTTTATT  TATAAATGTA  CTACCTGCGC  TAGCGCAGGC         300

CAGAAGAGGC  GCGTTGCCCA  AGTAACGGTG  TTGGAGGAGC  CAGTCCTGTG  ATAACACCTG         360

AGGGGGTGCA  TCGCCGAGGT  GATTGAACGG  CTGGCCACGT  TCATCATCGG  CTAAGGGGC          420

TGAATCCCCT  GGGTTGTCAC  CAGAAGCGTT  CGCAGTCGGG  CGTTTCGCAA  GTGGTGGAGC         480

ACTTCTGGGT  GAAAATAGTA  GCGAAGTATC  GCTCTGCGCC  CACCCGTCTT  CCGCTCTTCC         540

CTTGTGCCAA  GGCTGAAAAT  GGATCCCCTG  ACACGAGGTA  GTT ATG TCT GAA ATT           595
                                               Met Ser Glu Ile
                                                1

GTT GTC TCC AAA TTT GGC GGT ACC AGC GTA GCT GAT TTT GAC GCC ATG              643
Val Val Ser Lys Phe Gly Gly Thr Ser Val Ala Asp Phe Asp Ala Met
 5              10                  15                  20

AAC CGC AGC GCT GAT ATT GTG CTT TCT GAT GCC AAC GTG CGT TTA GTT              691
Asn Arg Ser Ala Asp Ile Val Leu Ser Asp Ala Asn Val Arg Leu Val
```

```
                                25                              30                              35
GTC CTC TCG GCT TCT GCT GGT ATC ACT AAT CTG CTG GTC GCT TTA GCT            739
Val Leu Ser Ala Ser Ala Gly Ile Thr Asn Leu Leu Val Ala Leu Ala
                40                              45                      50

GAA GGA CTG GAA CCT GGC GAG CGA TTC GAA AAA CTC GAC GCT ATC CGC            787
Glu Gly Leu Glu Pro Gly Glu Arg Phe Glu Lys Leu Asp Ala Ile Arg
            55                              60                      65

AAC ATC CAG TTT GCC ATT CTG GAA CGT CTG CGT TAC CCG AAC GTT ATC            835
Asn Ile Gln Phe Ala Ile Leu Glu Arg Leu Arg Tyr Pro Asn Val Ile
        70                              75                      80

CGT GAA GAG ATT GAA CGT CTG CTG GAG AAC ATT ACT GTT CTG GCA GAA            883
Arg Glu Glu Ile Glu Arg Leu Leu Glu Asn Ile Thr Val Leu Ala Glu
85                              90                      95                      100

GCG GCG GCG CTG GCA ACG TCT CCG GCG CTG ACA GAT GAG CTG GTC AGC            931
Ala Ala Ala Leu Ala Thr Ser Pro Ala Leu Thr Asp Glu Leu Val Ser
                    105                         110                     115

CAC GGC GAG CTG ATG TCG ACC CTG CTG TTT GTT GAG ATC CTG CGC GAA            979
His Gly Glu Leu Met Ser Thr Leu Leu Phe Val Glu Ile Leu Arg Glu
            120                         125                     130

CGC GAT GTT CAG GCA CAG TGG TTT GAT GTA CGT AAA GTG ATG CGT ACC           1027
Arg Asp Val Gln Ala Gln Trp Phe Asp Val Arg Lys Val Met Arg Thr
        135                         140                     145

AAC GAC CGA TTT GGT CGT GCA GAG CCA GAT ATA GCC GCG CTG GCG GAA           1075
Asn Asp Arg Phe Gly Arg Ala Glu Pro Asp Ile Ala Ala Leu Ala Glu
    150                         155                     160

CTG GCC GCG CTG CAG CTG CTC CCA CGT CTC AAT GAA GGC TTA GTG ATC           1123
Leu Ala Ala Leu Gln Leu Leu Pro Arg Leu Asn Glu Gly Leu Val Ile
165                         170                     175                     180

ACC CAG GGA TTT ATC GGT AGC GAA AAT AAA GGT CGT ACA ACG ACG CTT           1171
Thr Gln Gly Phe Ile Gly Ser Glu Asn Lys Gly Arg Thr Thr Thr Leu
                    185                     190                     195

GGC CGT GGA GGC AGC GAT TAT ACG GCA GCC TTG CTG GCG GAG GCT TTA           1219
Gly Arg Gly Gly Ser Asp Tyr Thr Ala Ala Leu Leu Ala Glu Ala Leu
                200                     205                     210

CAC GCA TCT CGT GTT GAT ATC TGG ACC GAC GTC CCG GGC ATC TAC ACC           1267
His Ala Ser Arg Val Asp Ile Trp Thr Asp Val Pro Gly Ile Tyr Thr
            215                     220                     225

ACC GAT CCA CGC GTA GTT TCC GCA GCA AAA CGC ATT GAT GAA ATC GCG           1315
Thr Asp Pro Arg Val Val Ser Ala Ala Lys Arg Ile Asp Glu Ile Ala
        230                     235                     240

TTT GCC GAA GCG GCA GAG ATG GCA ACT TTT GGT GCA AAA GTA CTG CAT           1363
Phe Ala Glu Ala Ala Glu Met Ala Thr Phe Gly Ala Lys Val Leu His
245                     250                     255                     260

CCG GCA ACG TTG CTA CCC GCA GTA CGC AGC GAT ATC CCG GTC TTT GTC           1411
Pro Ala Thr Leu Leu Pro Ala Val Arg Ser Asp Ile Pro Val Phe Val
                265                     270                     275

GGC TCC AGC AAA GAC CCA CGC GCA GGT GGT ACG CTG GTG TGC AAT AAA           1459
Gly Ser Ser Lys Asp Pro Arg Ala Gly Gly Thr Leu Val Cys Asn Lys
            280                     285                     290

ACT GAA AAT CCG CCG CTG TTC CGC GCT CTG GCG CTT CGT CGC AAT CAG           1507
Thr Glu Asn Pro Pro Leu Phe Arg Ala Leu Ala Leu Arg Arg Asn Gln
        295                     300                     305

ACT CTG CTC ACT TTG CAC AGC CTG AAT ATG CTG CAT TCT CGC GGT TTC           1555
Thr Leu Leu Thr Leu His Ser Leu Asn Met Leu His Ser Arg Gly Phe
    310                     315                     320

CTC GCG GAA GTT TTC GGC ATC CTC GCG CGG CAT AAT ATT TCG GTA GAC           1603
Leu Ala Glu Val Phe Gly Ile Leu Ala Arg His Asn Ile Ser Val Asp
325                     330                     335                     340

TTA ATC ACC ACG TCA GAA GTG AGC GTG GCA TTA ACC CTT GAT ACC ACC           1651
Leu Ile Thr Thr Ser Glu Val Ser Val Ala Leu Thr Leu Asp Thr Thr
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 345 |     |     |     |     | 350 |     |     |     |     |     | 355 |     |     |      |
| GGT | TCA | ACC | TCC | ACT | GGC | GAT | ACG | TTG | CTG | ACG | CAA | TCT | CTG | CTG | ATG | 1699 |
| Gly | Ser | Thr | Ser | Thr | Gly | Asp | Thr | Leu | Leu | Thr | Gln | Ser | Leu | Leu | Met |      |
|     |     | 360 |     |     |     |     | 365 |     |     |     |     | 370 |     |     |     |      |
| GAG | CTT | TCC | GCA | CTG | TGT | CGG | GTG | GAG | GTG | GAA | GAA | GGT | CTG | GCG | CTG | 1747 |
| Glu | Leu | Ser | Ala | Leu | Cys | Arg | Val | Glu | Val | Glu | Glu | Gly | Leu | Ala | Leu |      |
|     |     | 375 |     |     |     |     | 380 |     |     |     |     | 385 |     |     |     |      |
| GTC | GCG | TTG | ATT | GGC | AAT | GAC | CTG | TCA | AAA | GCC | TGC | GGC | GTT | GGC | AAA | 1795 |
| Val | Ala | Leu | Ile | Gly | Asn | Asp | Leu | Ser | Lys | Ala | Cys | Gly | Val | Gly | Lys |      |
|     | 390 |     |     |     |     | 395 |     |     |     |     | 400 |     |     |     |     |      |
| GAG | GTA | TTC | GGC | GTA | CTG | GAA | CCG | TTC | AAC | ATT | CGC | ATG | ATT | TGT | TAT | 1843 |
| Glu | Val | Phe | Gly | Val | Leu | Glu | Pro | Phe | Asn | Ile | Arg | Met | Ile | Cys | Tyr |      |
| 405 |     |     |     |     | 410 |     |     |     |     | 415 |     |     |     |     | 420 |      |
| GGC | GCA | TCC | AGC | CAT | AAC | CTG | TGC | TTC | CTG | GTG | CCC | GGC | GAA | GAT | GCC | 1891 |
| Gly | Ala | Ser | Ser | His | Asn | Leu | Cys | Phe | Leu | Val | Pro | Gly | Glu | Asp | Ala |      |
|     |     |     |     | 425 |     |     |     |     | 430 |     |     |     |     | 435 |     |      |
| GAG | CAG | GTG | GTG | CAA | AAA | CTG | CAT | AGT | AAT | TTG | TTT | GAG | TAAATACTGT |  |  | 1940 |
| Glu | Gln | Val | Val | Gln | Lys | Leu | His | Ser | Asn | Leu | Phe | Glu |     |     |     |      |
|     |     | 440 |     |     |     |     | 445 |     |     |     |     |     |     |     |     |      |

| | |
|---|---|
| ATGGCCTGGA AGCTATATTT CGGGCCGTAT TGATTTTCTT GTCACTATGC TCATCAATAA | 2000 |
| ACGAGCCTGT ACTCTGTTAA CCAGCGTCTT TATCGGAGAA TAATTGCCTT TAATTTTTT | 2060 |
| ATCTGCATCT CTAATTAATT ATCGAAAGAG ATAAATAGTT AAGAGAAGGC AAAATGAATA | 2120 |
| TTATCAGTTC TGCTCGCAAA GGAATTC | 2147 |

(2) INFORMATION FOR SEQ ID NO:2:

(i) SEQUENCE CHARACTERISTICS:
      (A) LENGTH: 449 amino acids
      (B) TYPE: amino acid
      (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Ser | Glu | Ile | Val | Val | Ser | Lys | Phe | Gly | Gly | Thr | Ser | Val | Ala | Asp |
| 1 | | | | 5 | | | | | 10 | | | | | 15 | |
| Phe | Asp | Ala | Met | Asn | Arg | Ser | Ala | Asp | Ile | Val | Leu | Ser | Asp | Ala | Asn |
| | | | 20 | | | | | 25 | | | | | 30 | | |
| Val | Arg | Leu | Val | Val | Leu | Ser | Ala | Ser | Ala | Gly | Ile | Thr | Asn | Leu | Leu |
| | | 35 | | | | | 40 | | | | | 45 | | | |
| Val | Ala | Leu | Ala | Glu | Gly | Leu | Glu | Pro | Gly | Glu | Arg | Phe | Glu | Lys | Leu |
| | 50 | | | | | 55 | | | | | 60 | | | | |
| Asp | Ala | Ile | Arg | Asn | Ile | Gln | Phe | Ala | Ile | Leu | Glu | Arg | Leu | Arg | Tyr |
| 65 | | | | | 70 | | | | | 75 | | | | | 80 |
| Pro | Asn | Val | Ile | Arg | Glu | Glu | Ile | Glu | Arg | Leu | Leu | Glu | Asn | Ile | Thr |
| | | | | 85 | | | | | 90 | | | | | 95 | |
| Val | Leu | Ala | Glu | Ala | Ala | Ala | Leu | Ala | Thr | Ser | Pro | Ala | Leu | Thr | Asp |
| | | | | 100 | | | | | 105 | | | | | 110 | |
| Glu | Leu | Val | Ser | His | Gly | Glu | Leu | Met | Ser | Thr | Leu | Leu | Phe | Val | Glu |
| | | | 115 | | | | | 120 | | | | | 125 | | |
| Ile | Leu | Arg | Glu | Arg | Asp | Val | Gln | Ala | Gln | Trp | Phe | Asp | Val | Arg | Lys |
| | | 130 | | | | | 135 | | | | | 140 | | | |
| Val | Met | Arg | Thr | Asn | Asp | Arg | Phe | Gly | Arg | Ala | Glu | Pro | Asp | Ile | Ala |
| | 145 | | | | | 150 | | | | | 155 | | | | 160 |
| Ala | Leu | Ala | Glu | Leu | Ala | Ala | Leu | Gln | Leu | Leu | Pro | Arg | Leu | Asn | Glu |
| | | | | 165 | | | | | 170 | | | | | 175 | |
| Gly | Leu | Val | Ile | Thr | Gln | Gly | Phe | Ile | Gly | Ser | Glu | Asn | Lys | Gly | Arg |

|     |     |     |     |     |     |     | 180 |     |     |     |     | 185 |     |     |     | 190 |     |
| --- | --- | --- | --- | --- | --- | --- | --- | --- | --- | --- | --- | --- | --- | --- | --- | --- | --- |

Thr Thr Thr Leu Gly Arg Gly Gly Ser Asp Tyr Thr Ala Ala Leu Leu
        195                 200             205

Ala Glu Ala Leu His Ala Ser Arg Val Asp Ile Trp Thr Asp Val Pro
    210                 215             220

Gly Ile Tyr Thr Thr Asp Pro Arg Val Val Ser Ala Ala Lys Arg Ile
225             230             235                 240

Asp Glu Ile Ala Phe Ala Glu Ala Ala Glu Met Ala Thr Phe Gly Ala
                245             250             255

Lys Val Leu His Pro Ala Thr Leu Leu Pro Ala Val Arg Ser Asp Ile
            260             265             270

Pro Val Phe Val Gly Ser Ser Lys Asp Pro Arg Ala Gly Gly Thr Leu
        275             280             285

Val Cys Asn Lys Thr Glu Asn Pro Pro Leu Phe Arg Ala Leu Ala Leu
    290             295             300

Arg Arg Asn Gln Thr Leu Leu Thr Leu His Ser Leu Asn Met Leu His
305             310             315             320

Ser Arg Gly Phe Leu Ala Glu Val Phe Gly Ile Leu Ala Arg His Asn
                325             330             335

Ile Ser Val Asp Leu Ile Thr Thr Ser Glu Val Ser Val Ala Leu Thr
            340             345             350

Leu Asp Thr Thr Gly Ser Thr Ser Thr Gly Asp Thr Leu Leu Thr Gln
        355             360             365

Ser Leu Leu Met Glu Leu Ser Ala Leu Cys Arg Val Glu Val Glu Glu
    370             375             380

Gly Leu Ala Leu Val Ala Leu Ile Gly Asn Asp Leu Ser Lys Ala Cys
385             390             395             400

Gly Val Gly Lys Glu Val Phe Gly Val Leu Glu Pro Phe Asn Ile Arg
                405             410             415

Met Ile Cys Tyr Gly Ala Ser Ser His Asn Leu Cys Phe Leu Val Pro
            420             425             430

Gly Glu Asp Ala Glu Gln Val Val Gln Lys Leu His Ser Asn Leu Phe
        435             440             445

Glu (2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:3:

CTTCCCTTGT GCCAAGGCTG        20

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

-continued (xi) SEQUENCE DESCRIPTION: SEQ ID NO:4:

GAATTCCTTT GCGAGCAG								18

METHOD FOR THE PRODUCTION OF L-THREONINE BY FERMENTATION, USING MUTATED DNA ENCODING ASPARTOKINASE III

This application is a 371 of PCT/JP93/01640, filed Nov. 10, 1993.

TECHNICAL FIELD

The present invention relates to the microbiological industry, and describes a method for the production of L-threonine by fermentation. L-threonine is an essential amino acid, and it is used as a component of various nutritional mixtures for medical purposes. Furthermore, it is used as a feed additive for animals, as a reagent in the pharmaceutical and chemical industries, and as a growth factor for the production of amino acids such as lysine and homoserine by microorganisms.

BACKGROUND ART

In the past, bacteria separated from the natural environment or artificial mutants of such bacteria have been used as microorganisms for the production of L-threonine by fermentation. Many L-threonine-producing artificial mutants are known, the majority of which are resistant to α-amino-β-hydroxyvaleric acid and belong to the genus Escherichia, Serratia, Brevibacterium or Corynebacterium. Regarding Escherichia, in JPA 55-131397, JPA 59-31691, JPA 56-15696 and JPW 3-501682 are there described methods for the production of L-threonine by bacteria transformed by recombinant plasmids containing threonine operons.

Also, of the heretofore known threonine-producing bacteria, *Escherichia coli* BKIIM (VKPM) B-3996 strain has exhibited the most superior level of threonine production and coefficient of consumption (JPW 3-501682). According to the present invention, "coefficient of consumption" refers to the number of grams of sugar required for the production of one gram of threonine. If this bacterium is cultured in an experimental fermenter, adding sugar-ammonia to the culture medium in response to the signals from the pH sensor, then the maximum degree of biosynthesis of threonine is 85 g/l, and the coefficient of consumption is 2 g of sugar per one gram of threonine.

Aspartokinase (hereunder abbreviated to AK) is an enzyme which converts aspartic acid to β-phosphoaspartic acid, and it is the main regulatory site of the biosynthesis pathway of aspartic acid and its derivative amino acids. As shown in FIG. 1, there are three types of AK from *E. coli* (AK I, AK II, AK III) and the first two of these are bifunctional enzymes having homoserine dehydrogenase (hereunder sometimes abbreviated to HD) activity. One of these is AK I-HD I which is coded for by the thrA gene, and the other is AK II-HD II which is coded for by the metL(M) gene.

Only AK III is a monofunctional enzyme, and it is the product of a gene named lysC, and is known to undergo repression and feedback inhibition by lysine. On the other hand, AK I undergoes concerted repression by threonine and isoleucine, and inhibition by threonine, while AK II undergoes repression by methionine. The proportion of the intracellular activities thereof is AK I:AK II:AK III= approximately 5:1:4.

The lysC gene of *E. coli* has already been cloned, and its base sequence has been determined (Cassan, M., Parsot, C., Cohen, G. N. and Patte. J. C., J. Biol. Chem., 261, 1052, 1986). Also, the production of L-threonine by fermentation using strains of *E. coli* whose AK III activity has been reinforced, is described by Mizukami, et al. (Mizukami, T. et al., Agric. Biol. Chem., 50, 1015, 1986). However, sufficient release of the lysine-dependent feedback inhibition on the AK III reported by Mizukami, et al. has not yet been achieved.

Thus, the subject matter of the present invention is obtaining AK III with sufficient release of the feedback inhibition due to lysine, and providing a method for the production of L-threonine by fermentation which is much improved over the prior art.

DISCLOSURE OF INVENTION

The inventors of the present invention, as a result of diligent research carried out to overcome the above mentioned problem, have succeeded in obtaining a gene (mutant lysC, or lysC*) which codes for AK III in *E. coli* and which sufficiently releases the feedback inhibition due to lysine, and have discovered that by introducing this gene into threonine-producing bacteria, L-threonine is efficiently accumulated, and thus the present invention has been completed.

In other words, the present invention relates to a DNA containing a gene which codes for aspartokinase III found in Escherichia bacteria and which has a mutation in the coding region which releases the feedback inhibition by lysine on the above mentioned aspartokinase III, and specifically, it relates to the above mentioned DNA in which the mutation which releases the feedback inhibition by lysine on aspartokinase III is positioned, e.g., on the A domain or B domain of aspartokinase III, and more specifically, it relates to the above mentioned DNA in which the mutation which releases the feedback inhibition by lysine on aspartokinase III is, with reference to the below mentioned Sequence Listing: SEQ ID NO: 1, selected from the group consisting, e.g., of a mutation wherein the 323rd Gly is replaced by Asp; a mutation wherein the 323rd Gly is replaced by Asp and the 408th Gly is replaced by Asp; a mutation wherein the 34th Arg is replaced by Cys and the 323rd Gly is replaced by Asp; a mutation wherein the 325th Leu is replaced by Phe; a mutation wherein the 318th Met is replaced by Ile; a mutation wherein the 318th Met is replaced by Ile and the 349th Val is replaced by Met; a mutation wherein the 345th Ser is replaced by Leu; a mutation wherein the 347th Val is replaced by Met; a mutation wherein the 352nd Thr is replaced by Ile; a mutation wherein the 352nd Thr is replaced by Ile and the 369th Ser is replaced by Phe; a mutation wherein the 164th Glu is replaced by Lys; and a mutation wherein the 417th Met is replaced by Ile and the 419th Cys is replaced by Tyr.

Furthermore, the present invention relates to the above mentioned DNA which is a recombinant DNA linked with vector DNA capable of autonomous replication in Escherichia bacteria. Also, it relates to microorganisms belonging to the genus Escherichia which have been transformed by the introduction of the above mentioned recombinant DNA into the cells. Also within the scope of the present invention are microorganisms which have been transformed by the introduction into their chromosomal DNA of the DNA which codes for the above mentioned Escherichia-derived aspartokinase III and contains a gene with a mutation in the coding region which releases the feedback inhibition by lysine on the above mentioned aspartokinase III.

The present invention also relates to a method for the production of L-threonine, characterized by culturing any of the above mentioned microorganisms in a fermentation medium, producing and accumulating L-threonine in the culture, and collecting the L-threonine from the culture.

A detailed description of the present invention will now be provided.

As the donor bacteria to supply the DNA containing the gene coding for AK III (lysC) may be used any microorganism belonging to the genus Escherichia. Specifically, those mentioned in the writings of Neidhardt (Neidhardt, F. C. et al., *Escherichia coli* and *Salmonella typhimurium*, American Society for Microbiology, Washington, D.C., 1208, Table 1). Examples thereof include *E. coli* strains JM109 and MC1061.

If a wild strain is used as the donor bacteria to supply the DNA containing the gene coding for AK III (lysC), then a DNA containing a wild type of the AK III gene may be obtained. For the introduction of a mutation into this gene in order to obtain an AK III gene which releases the feedback inhibition due to L-lysine (lysC*), in vitro mutation of the DNA may be effected by direct treatment with hydroxylamine. Hydroxylamine is a chemical mutating agent which induces a mutation C→T by converting cytosine to $N^4$-hydroxycytosine.

Further, a DNA containing the AK III gene which releases the feedback inhibition due to L-lysine may be obtained by using as a DNA donor strain a mutant which releases the feedback inhibition on AK III activity due to L-lysine. This mutant may be obtained from cells which have been subjected to, for example, a conventional method for mutating treatment, exposure to ultraviolet rays or treatment with a mutating agent such as N-methyl-N'-nitro-N-nitrosoguanidine (NTG).

A description will now be provided regarding the preparation of a DNA containing a gene which codes for AK III (lysC). First, *E. coli* having a wild type of lysC, for example, MC1061 strain, is cultured to obtain cultured cells. The culturing of the above mentioned microorganism may be carried out by a conventional solid culture method, but a liquid culture method is preferably used for the culturing from the view point of cell collection. Also, the culture medium may be one prepared for example, by adding one or more inorganic salts such as monopotassium phosphate ($KH_2PO_3$), dipotassium phosphate ($K_2HPO_3$), magnesium sulfate, sodium chloride, magnesium chloride, ferric chloride, ferric sulfate, or manganese sulfate, to one or more nitrogen sources such as yeast extract, peptone, beef extract, corn steep liquor or an effusion of soybean or wheat, and then further adding carbohydrates, vitamins, etc., if necessary. The initial pH of the culture medium is appropriately adjusted to 7–8. Also, the culturing is carried out at 30°–42° C., and preferably about 37° C., for 4–24 hours, by submerged culture with aeration and stirring, shaking culture, standing culture, or the like. The cultured product which is obtained in this manner is subjected to centrifugal separation at, for example, 3,000 rpm for 5 minutes, to obtain cells of *E. coli* MC1061 strain.

Chromosomal DNA may be obtained from these cells by, for example, the method of Saito and Miura (Biochem. Biophys. Acta. 72, 619, 1963), the method of K. S. Kirby (Biochem. J. 64, 405, 1956), etc.

For isolating the lysC gene, the chromosomal DNA obtained by the above methods is cleaved using an appropriate restriction enzyme. If the degree of cleavage is controlled by controlling the cleavage reaction time, etc., then a wide variety of restriction enzymes may be used. Next, the gene may be linked to a vector DNA which is capable of replication in Escherichia bacteria, and the resulting recombinant DNA may be used to transform a mutant strain of Escherichia, for example, GT3, which lacks aspartokinase I, II and III (to create a gene library), and of the resulting transformants may be isolated a strain which has become capable of growing on a minimal culture medium without lysine, thus separating the recombinant DNA containing the lysC gene.

Concretely, a chromosomal DNA is subjected to digestion with a restriction enzyme, for example, Sau3AI at a temperature of 30° C. or higher, and preferably 37° C., at an enzyme concentration of 1–10 units/ml for various times (1 minute–2 hours) for complete digestion or partial digenstion to obtain a mixture containing a variety of chromosomal DNA fragments. The vector DNA which is capable of replication in Escherichia bacteria is subjected to digestion with a restriction enzyme, for example, BamHI, which produces the same terminal base sequence as does the restriction enzyme Sau3A used for the cleavage of the chromosomal DNA, at a temperature of 30° C. or higher, at an enzyme concentration of 1–100 units/ml for 1 hour or more, and preferably 1–3 hours, to effect complete digestion thereof to obtain the cleaved DNA. Next, the mixture containing the DNA fragments which were derived from *E. coli* MC1061 and include the lysC gene prepared in the manner described above, is mixed with the cleaved vector DNA, and a DNA ligase, preferably T4 DNA ligase, is allowed to act thereon at a temperature of 4°–16° C., at an enzyme concentration of 1–100 units/ml for 1 hour or more, preferably 6–24 hours, to obtain a recombinant DNA.

The vector DNA to be used according to the present invention is preferably a plasmid vector DNA, for example, pUC19, pUC18, pBR322, pHSG299, pHSG399, RSF1010, etc. In addition, phage DNA vectors may be used. Promoters which function in microorganisms, for example, lac, trp, PL and the like may be used for en efficient expression of the gene which is useful for the desired purpose. The term "recombinant DNA" used here includes DNA resulting from the incorporation of the above gene into chromosomes by methods which make use of transposons (Berg, D. E. and Berg, C. M., Bio/Technol., 1, 417, 1983), Mu phage (Japanese Patent Application Disclosure HEI 2-109985) or homologous recombination (Experiments in Molecular Genetics, Cold Spring Harbor Lab., 1972).

This recombinant DNA is used to transform, for example, *E. coli* K-12 strain, and preferably GT3 strain, etc., and then a strain which has recombinant DNA containing the lysC gene is obtained from the strains having an increased level of AK activity or from strains with complimented nutritional requirements. The transformation may be carried out according to the method of D. M. Morrison (Methods in Enzymology, 68, 326, 1979) or a method whereby the recipient cells are treated with calcium chloride to raise the degree of penetration of the DNA (Mandel, M. and Higa, A., J. Mol. Biol., 53, 159, 1970). Then, the recombinant DNA prepared by the insertion of DNA containing the lysC gene into the vector DNA may be isolated from the above mentioned strains following, for example, the method of P. Guerry, et al. (J. Bacteriol., 116, 1064, 1973) or the method of D. B. Clewell (J. Bacteriol., 110, 667, 1972).

It may be confirmed that the candidate strain in fact possesses the recombinant DNA having lysC, by preparing a cell extract solution, and then preparing therefrom a crude enzyme solution for confirmation of aspartokinase activity. The method of measuring the enzyme activity of aspartokinase may be according to the method of Stadtman, et al. (Stadtman, E. R., Cohen, G. N., LeBras, G., and Robichon-Szulmajster, H., J. Biol. CHem., 236, 2033, 1961).

Alternatively, the lysC gene may be obtained by amplifying the lysC gene from the chromosomal DNA obtained by the method of Saito and Miura, by the PCR (polymerase chain reaction; see White, T. J. et al., Trends Genet. 5, 185, 1989). The DNA primer to be used for the amplification is one which is complementary to the 3' ends of the double stranded DNA containing an entire region of the lysC gene or a segment thereof. If only a portion of the lysC gene is to be amplified, then the gene library must be screened for DNA fragments containing the entire region, using the DNA fragment as the primer. If the entire region is to be amplified, then the DNA fragment may be subjected to agarose gel electrophoresis, and then the desired band is cut out to recover the DNA fragment containing the lysC gene.

The DNA primer may be appropriately prepared based on, for example, a known sequence of E. coli (Cassan, M., Parsot, C., Cohen, G. N. and Patte, J. C., J. Biol. Chem., 261, 1052, 1986), and preferred are the two types of primers, 5'-CTTCCCTTGTGCCAAGGCTG- 3' (SEQ ID NO: 2) and 5'-GAATTCCTTTGCGAGCAG-3' (SEQ ID NO: 3), which are capable of amplifying the 1347-base region coding for the lysC gene. The synthesis of the DNA may be carried out in a conventional manner, using a DNA synthesizer Model 380B, produced by Applied Biosystems Co., and the phosphoamidide method (see Tetrahedron Letters, 22, 1859, 1981). The PCR reaction may be carried out using a DNA thermal cycler Model PJ2000, produced by Takara Shuzo Co., and Taq DNA polymerase, produced by Takara Shuzo Co., following the method indicated by the supplier.

The lysC gene which has been amplified by the PCR method is linked to vector DNA which is capable of replication in Escherichia bacteria, and it is introduced into cells thereof. The method of transforming a host with the vector DNA to be used and the method of confirming the presence of lysC are the same as those described previously.

The method of inducing mutations into the obtained lysC, such as the substitution, insertion or deletion of amino acids, may be effected by the recombinant PCR method (Higuchi, R., 61, in PCR Technology (Erlich, H. A., Eds., Stockton Press, 1989)), the site-directed mutagenesis method (Kramer, W. and Frits, H. J., Meth. in Enzymol., 154, 350, 1987; Kunkel, T. A. et al., Meth. in Enzymol., 154, 367, 1987), etc. By using these methods, a desired mutation may be induced at a desired site. Furthermore, for the introduction of random mutation may be used a method of directly treating the object gene on chromosome DNA or a plasmid with hydroxylamine (Hashimoto, T. and Sekiguchi, M., J. Bacteriol., 159, 1039, 1984); a conventional method involving exposure of cells containing the object DNA to ultraviolet rays or to treatment with a chemical agent such as N-methyl-N'-nitrosoguanidine, nitrous acid, or the like; or a method of chemically synthesizing the object gene.

The method of selecting the inhibition-releasing mutant gene lysC* involves, at first, transforming with the mutated recombinant DNA an AK-deficient strain, for example, E. coli GT3 strain. Next, the transformant is cultured in a minimal medium, for example, M9, containing a significant amount of lysine. The strains which possess plasmids having the wild type of lysC exhibit the inhibition by lysine of AK III which is the only AK in the strain, and therefore the synthesis of threonine, isoleucine, methionine and diaminopimeric acid (DAP) is no longer possible and growth is inhibited. In contrast, the strains which possess plasmids having lysC* which releases the inhibition by lysine should be capable of growing on a minimal medium containing a significant amount of lysine. Utilizing this phenomenon, the desired strains, that is, strains with plasmids having the lysC* which releases the inhibition, i.e., those which are resistant to lysine or to S-2-aminoethylcysteine (AEC), an analogue of lysine, may be selected.

The above mentioned mutant gene obtained in this manner may be used as the recombinant DNA for introduction into an appropriate microorganism (host) and expressed therein to obtain a microorganism possessing AK with release of the feedback inhibition.

The above mentioned wild strains of Escherichia bacteria may be mentioned as hosts into which the obtained lysC gene or mutant lysC gene (lysC*) is to be introduced and then amplified for the production of threonine, but in addition to these, any other bacteria may be used as hosts provided that both the replication origin of the recombinant vector DNA constructed here and the lysC gene or the mutated lysC gene (lysC*) function therein, the recombinant vector DNA is capable of replication therein, and the lysC gene or the mutated lysC gene (lysC*) may be reinforced therein. The most preferable host is E. coli B-3996 strain.

The transformants obtained in the above manner, which possess the recombinant vector DNA containing the gene which codes for aspartokinase III with release of the feedback inhibition due to lysine, are cultured, and the object L-threonine is produced and accumulated in the culture solution and then collected.

The culture medium to be used for the production of L-threonine is a conventional culture medium containing a carbon source, a nitrogen source, inorganic ions, and if necessary other organic components.

The carbon source to be used may be a saccharide such as glucose, lactose, galactose, fructose, a hydrolyzed starch, an alcohol such as glycerol or sorbitol, or an organic acid such as fumaric acid, citric acid, succinic acid, or the like.

The nitrogen source to be used may be an inorganic ammonium salt such as ammonium sulfate, ammonium chloride, ammonium phosphate, etc., an organic nitrogen such as soybean hydrolysate, or ammonia gas, ammonia water, or the like.

A required substance such as vitamin B1, L-homoserine or the like, or yeast extract, is preferably added in an appropriate amount as an organic trace nutrient source. In addition to these, potassium phosphate, magnesium sulfate, iron ion, manganese ion, etc. are added in small amounts if necessary.

The culturing is preferably carried out under aerobic conditions for 16–72 hours, while the culturing temperature is controlled to 25° C.–45° C., and the pH of the culture to 5–8. For the control of the pH, an inorganic or organic acid, alkali substance, or ammonia gas, etc. may be used. The collection of the L-threonine from the fermentated mash is carried out by combining the conventional ion exchange resin method, precipitation method and any other publicly known methods.

BRIEF DESCRIPTION OF THE DRAWINGS

FIG. 7 shows the points of mutation of each LysC* (See Example 5 (5-3) see amino acid residues 295–374 of SEQ ID NO:1.).

BEST MODE FOR CARRYING OUT THE INVENTION

A more concrete description of the present invention is provided below, with reference to the Examples.

EXAMPLE 1

Cloning of the wild lysC gene

The base sequence of the lysC gene of *E. coli* has already been reported (Cassan, M., Parsot, C., Cohen, G. N. and Patte, J. C., J. Biol. Chem., 261, 1052, 1986), and it is known that its open reading frame (ORF) has 1,347 bases coding for 449 amino acids. Since an operator is present which is responsible for repression by lysine, this operator region was removed, and the cloning was effected by amplifying only the region containing the SD sequence and the ORF, using the PCR method.

Figure 1:
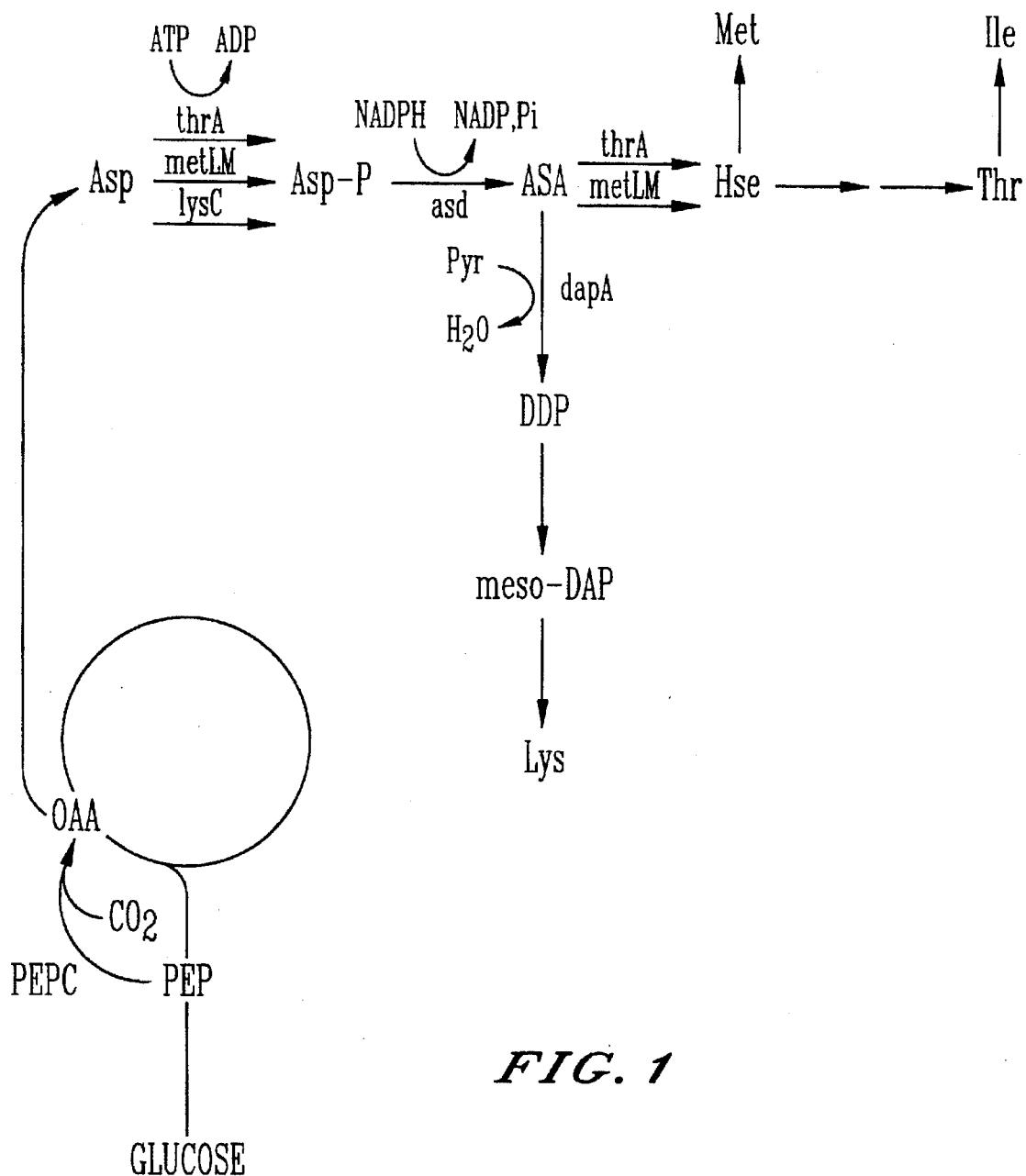
FIG. 1 is a schematic diagram of the biosynthetic pathway of threonine.
Figure 2B:
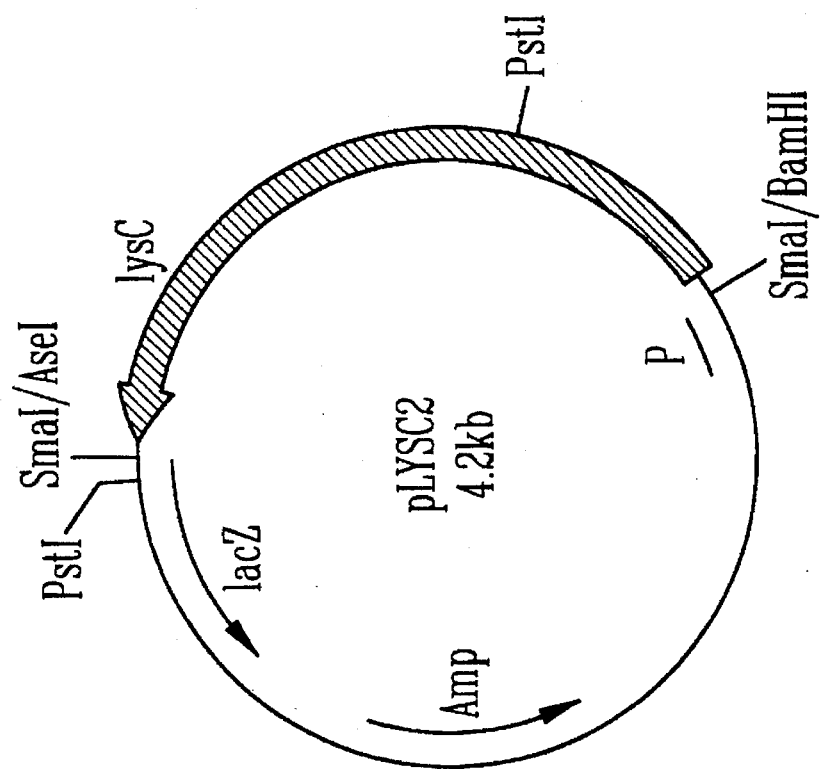
FIG. 2 is a restriction enzyme map for pLYSC1 and pLYSC2 (See Example 1).
Figure 2A:
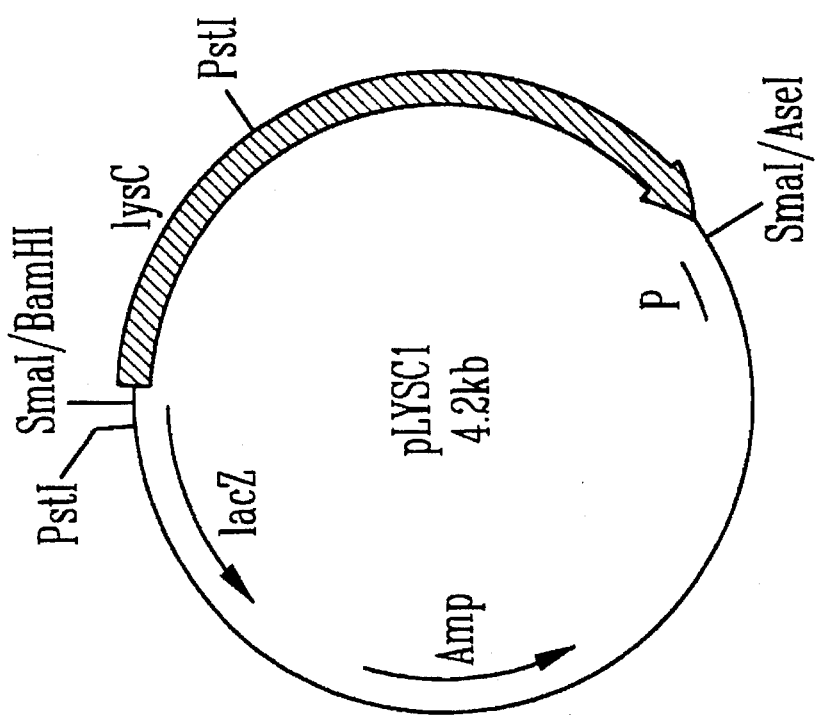

Two different primers, 5'-CTTCCCTTGTGCCAAGGCTG-3' (Sequence No. 2) and 5'-GAATTCCTTTGCGAGCAG-3' (Sequence No. 3) were prepared, and the entire genomic DNA of *E. coli* K-12 MC1061 strain was recovered using the method of Saito and Miura (Biochem. Biophys. Acta., 72, 619, 1963). These were used in a PCR reaction according to the method of Erlich, et al. (PCR Technology, Stockton Press, 1989) to amplify the object DNA. The resulting DNA was digested with BamHI and AseI, and then the ends thereof were made blunt and the DNA was inserted into the SmaI site of the multicopy vector pUC18. Thus were obtained two types of plasmids, one antisense (pLYSC1) and one sense (pLYSC2) with respect to the lacZ promoter (FIG. 2).

These plasmids were used for transformation of *E. coli* GT3 strains (thrA1016$^b$, metLM1005, lysC1004) completely deficient in AK I, II and III, and since the homoserine+diaminopimeric acid requirements of GT3 were complemented, this confirmed that the gene was lysC which codes for the active AK III.

EXAMPLE 2

Acquisition of inhibition-released mutant gene lysC*

(2-1);

To efficiently obtain an inhibition-released lysC gene (lysC*), the gene on the recombinant plasmid DNA prepared in Example 1 was subjected to mutating treatment.

As a method of obtaining the inhibition-released mutant gene lysC*, first the wild lysC recombinant plasmid was incorporated for transformation into the completely AK-deficient *E. coli* GT3. A significant amount of lysine was added to an M9 minimal medium having the composition listed in Table 1 below, and the transformants were cultured in the medium. The strains possessing plasmids having the wild type of lysC exhibited inhibition of the only AK, i.e., AK III, by lysine, and therefore the synthesis of threonine, isoleucine, methionine and diaminopimeric acid (DAP) was no longer possible and growth was inhibited.

TABLE 1

| M9 minimal medium | | |
|---|---|---|
| A: | 20 × M9 | (g/l) |
| | Na$_2$HPO$_4$.12H$_2$O | 303 |
| | KH$_2$PO$_4$ | 60 |
| | NaCl | 10 |
| | NH$_4$Cl | 20 |
| B: | 1 M MgSO$_4$ | |
| C: | 50% glucose | |
| D: | 1 g/l thiamine | |

A, B, C, D and water were sterilized separately and mixed at a ratio of A:B:C:D:water = 5:0.1:1:0.1:95.

In contrast, the strains which possess plasmids having lysC* which release the inhibition by lysine are expected to be capable of growth in a minimal medium containing a significant amount of lysine. Utilizing this phenomenon, selection was made of strains whose growth was resistant to lysine or to S-2-aminoethylcysteine (AEC), an analogue of lysine, i.e., those strains with plasmids having the lysC* which releases the inhibition.

(2-2); Investigation of the conditions of selection of the feedback inhibition-resistant lysC mutants (lysC*)

First, pLYSC1 and pLYSC2 were each incorporated into *E. coli* GT3 for its transformation to obtain two different transformants, and culturing was effected on an M9 minimal agar plate medium containing lysine or AEC. Also, the growth inhibition concentration of lysine or AEC was determined, and the conditions for selection of lysC* were investigated.

As shown in Table 2, it was clear that with respect to pLYSC2 the amount of expression was amplified by the lacZ promoter, and thus there was resistance to a considerably high concentration of lysine or AEC even with the wild type of lysC, but that since the lysC gene of pLYSC1 was antisense with respect to the lacZ promoter and the promoter of the LysC gene itself was lacking, the amount of expression was low and the growth was inhibited under a lower concentration of lysine or AEC (growth was completely inhibited by addition of either lysine or AEC at about 0.2 mM. The "+" in the table indicates growth of the transformant, and the "−" indicates no growth thereof). This growth inhibition was found to be restored by the simultaneous addition of homoserine and DAP.

TABLE 2

Relationship between growth of completely AK-deficient GT3 strain possessing lysC plasmid and concentration of added lysine or lysine analogue AEC (a): Lys concentration and growth

|  | 0 | 0.2 | 0.4 | 0.8 | 1.5 | 3 | 6 | 12 | 25 | 50 | 100 | 200 | (mM) |
|---|---|---|---|---|---|---|---|---|---|---|---|---|---|
| GT3/pLYSC1 | + | - | - | - | - | - | - | - | - | - | - | - | |
| GT3/pLYSC2 | + | + | + | + | + | + | + | + | + | + | ± | - | |

(b): AEC concentration and growth

|  | 0 | 0.2 | 0.4 | 0.8 | 1.5 | 3 | 6 | 12 | 25 | 50 | (mM) |
|---|---|---|---|---|---|---|---|---|---|---|---|
| GT3/pLYSC1 | + | - | - | - | - | - | - | - | - | - | |
| GT3/pLYSC2 | + | ± | ± | ± | ± | ± | - | - | - | - | |

M9 agar medium, 37° C., 2 day culturing
+: growth, ±: some growth, -: no growth

Thus, pLYSC1 was used for the mutation introduction experiment, and the selection medium used for selection of the lysC* was prepared by adding 10 mM of lysine or 0.2 mM of AEC to the M9 minimal medium.

(2-3); Mutating treatment

Hydroxylamine is a chemical mutating agent which induces a mutation of C→T by converting cytosine to $N^4$-hydroxycytosine. For the introduction of the mutation into the plasmid, two methods were used, one an in vitro mutating treatment method whereby the plasmid was treated directly with hydroxylamine, and the other an in vivo mutating treatment method to provide variety to the mutation, i.e., for mutations other than C→T, whereby cells possessing the plasmids are treated with nitrosoguanidine (NTG) and then the plasmids are extracted.

(2-4); In vitro mutating treatment with hydroxylamine

Figure 3:
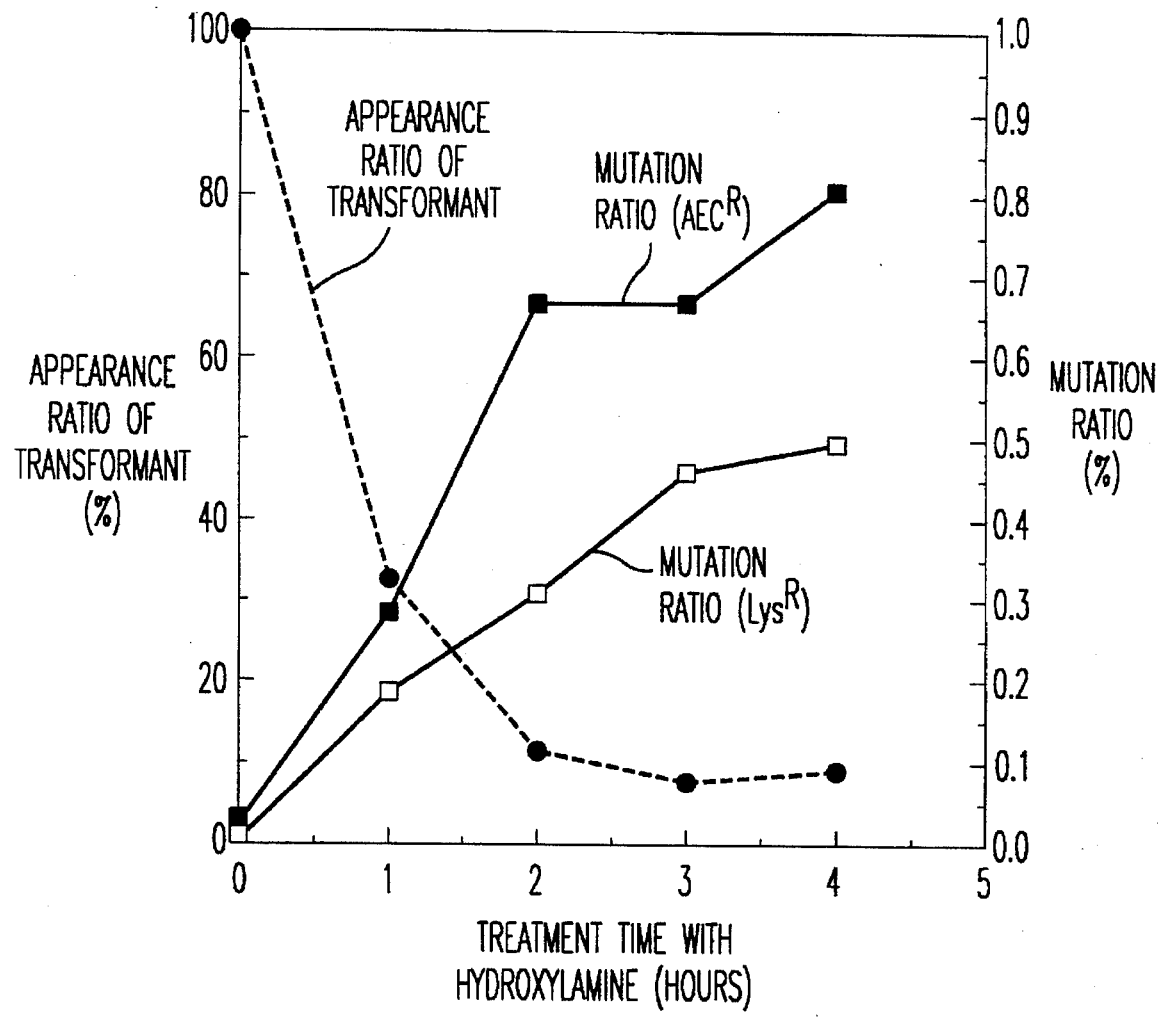
FIG. 3 is a graph showing the effects of the introduction of hydroxylamine-induced mutations on lysC (See Example 2 (2-4)).

A 2 μg portion of the DNA was treated in a reaction solution shown in Table 3 below, i.e., in 0.4M of hydroxylamine at 75° C. for 1–4 hours. The treated DNA was purified with glass powder, and then used for the transformation into a completely AK-deficient GT3 strain, which was plated onto a complete medium (L-broth; 1% bacto trypton, 0.5% yeast extract, 0.5% NaCl, 1.5% agar) to form colonies. The formed colonies were replicated onto the selection medium obtained in (2-1). The ratio of appearance of the transformants and the mutation ratio varied as shown in FIG. 3. With 4 hours of treatment, the yield of the mutant strain was 0.5–0.8%, which is a rather high value.

TABLE 3

| Reaction solution composition | |
|---|---|
| 0.1 M $KH_2PO_4$ - 1 mM EDTA (pH 6.0) | 100 μl |
| 1 M hydroxylamine - 1 mM EDTA (pH 6.0) | 80 μl |
| DNA | 2 μg |
| Water | balance |
| Total | 200 μl |

(2-5); In vivo mutating treatment with nitrosoguanidine (NTG)

pLYSC1 was used for transformation of *E. coli* MC1061, and the cells were directly subjected to treatment with NTG. The treated cells were cultured overnight for fixation of the mutation, after which the plasmids were extracted therefrom, and used for transformation into GT3, and screening was carried out in the same manner as in (2-4) to obtain lysine resistant ($Lys^R$) or AEC resistant ($AEC^R$) mutants. The treatment is outlined in Table 4 below.

Table 4: Outline of treatment (1) Culturing of cells containing the object plasmid in a 2×TY medium (1.6% bacto trypton, 1% yeast extract, 0.5% NaCl), followed by cell collection at O.D. 660 nm=approx. 0.3.

(2) Washing with TM buffer.

(3) Suspension in NTG solution (0.2 mg/ml in TM buffer), followed by treatment at 37° C. for 0–90 minutes.

(4) Washing with TM buffer and 2×TY medium, followed by culturing overnight in 2×TY medium and fixation of mutation.

(5) Extraction of plasmid DNA from cells, transformation of the GT3 strain, and screening for recombinant strains.

The composition of the TM buffer was as follows;

| Tris | 50 mM |
|---|---|
| Maleic acid | 50 mM |
| $(NH_4)_2SO_4$ | 1 g/l |
| $MgSO_4 \cdot 7H_2O$ | 0.1 g/l |
| $Ca(NO_3)_2$ | 5 mg/l |
| $FeSO_4 \cdot 7H_2O$ | 0.25 mg/l |

Adjusted to pH 6.0 using NaOH.

EXAMPLE 3

Isolation of lysC gene (3-1);

A total of 180 candidate strains obtained in Example 2 (hydroxylamine-treated=48 strains, and NTG-treated=132 strains) were again spotted onto a selection medium, and the presence of AEC or lysine resistance was confirmed to obtain 153 strains. Taking note of the difference in the patterns of amino acid accumulation in the medium, the 153 strains were separated into 14 groups and a representative of each group was selected for the measurement of AK activity. Since there was no great difference between the mutants treated with hydroxylamine and those treated with NTG, the experiment was continued without distinction between the two.

(3-2); Measurement of aspartokinase activity

A completely AK-deficient GT3 strain was used as the host in respect of which the above mentioned 14 mutant pLYSC1's (named the pLYSC1* series) and wild pLYSC1 plasmids were respectively used for transformation, after which a cell-free extract was prepared from the transformants and the enzyme activity of AK III was measured. The method for the measurement of the enzyme activity was as follows.

(3-3); Measurement method for AK III activity (3-3-1); Method for preparation of crude enzyme solution (1) Culturing of cells in 2×TY medium, followed by cell collection at O.D. 660 nm=approx. 0.8.

(2) Washing with 0.02M $KH_2PO_4$ (pH 6.75)—0.03M β mercaptoethanol at 0° C.

(3) Sonic crushing of cells (0° C., 100 W, 30 sec×4 times).

(4) Centrifugation at 0° C., 33 krpm for 1 hour, followed by addition of ammonium sulfate to supernatant to 80% saturation.

(5) Centrifugation, followed by dissolution of pellets in buffer of (2), and preservation (−20° C.).

(3-3-2); Method for measurement of enzyme activity

The method of measuring the enzyme activity was according to the method of Stadtman, et al. (Stadtman, E. R., Cohen, G. N., Lebras, G. and Robichon-Szulmajster, H., J. Biol. Chem., 236, 2033, 1961).

The reaction solution had the composition shown in Table 5 below.

TABLE 5

| Reaction solution composition | |
|---|---|
| Reaction mixture*1 | 0.3 ml |
| Hydroxylamine solution*2 | 0.2 ml |
| 0.1 M potassium aspartate (pH 7.0) | 0.1 ml |
| Enzyme solution | |
| Water | balance |
| Total | 1.0 ml |

*1: 9 ml of 1 M Tris-HCl (pH 8.1) + 0.5 ml of 0.3 M $MgSO_4$ 4 + 5 ml of 0.2 M ATP (pH 7.0)
*2: 8 M hydroxylamine neutralized with KOH just prior to use
The reaction solution without potassium aspartate is defined as blank.

The measurement method is outlined in Table 6 below.

Table 6: Outline of measurement method (1) Incubation of the reaction solution at 27° C. for 45 minutes.

(2) Addition of an $FeCl_3$ solution (0.4 ml of 2.8N HCl+0.4 ml of 12% TCA+0.7 ml of 5% $FeCl_3.6H_2O$/0.1N HCl) for coloration.

(3) Centrifugation, followed by measurement of absorbance value at 540 nm ($A_{540}$) of supernatant.

The activity was expressed as the amount of hydroxamic acid produced during one minute.

1 U=1 μmol/min. Molar absorbance coefficient=600.

Figure 4:
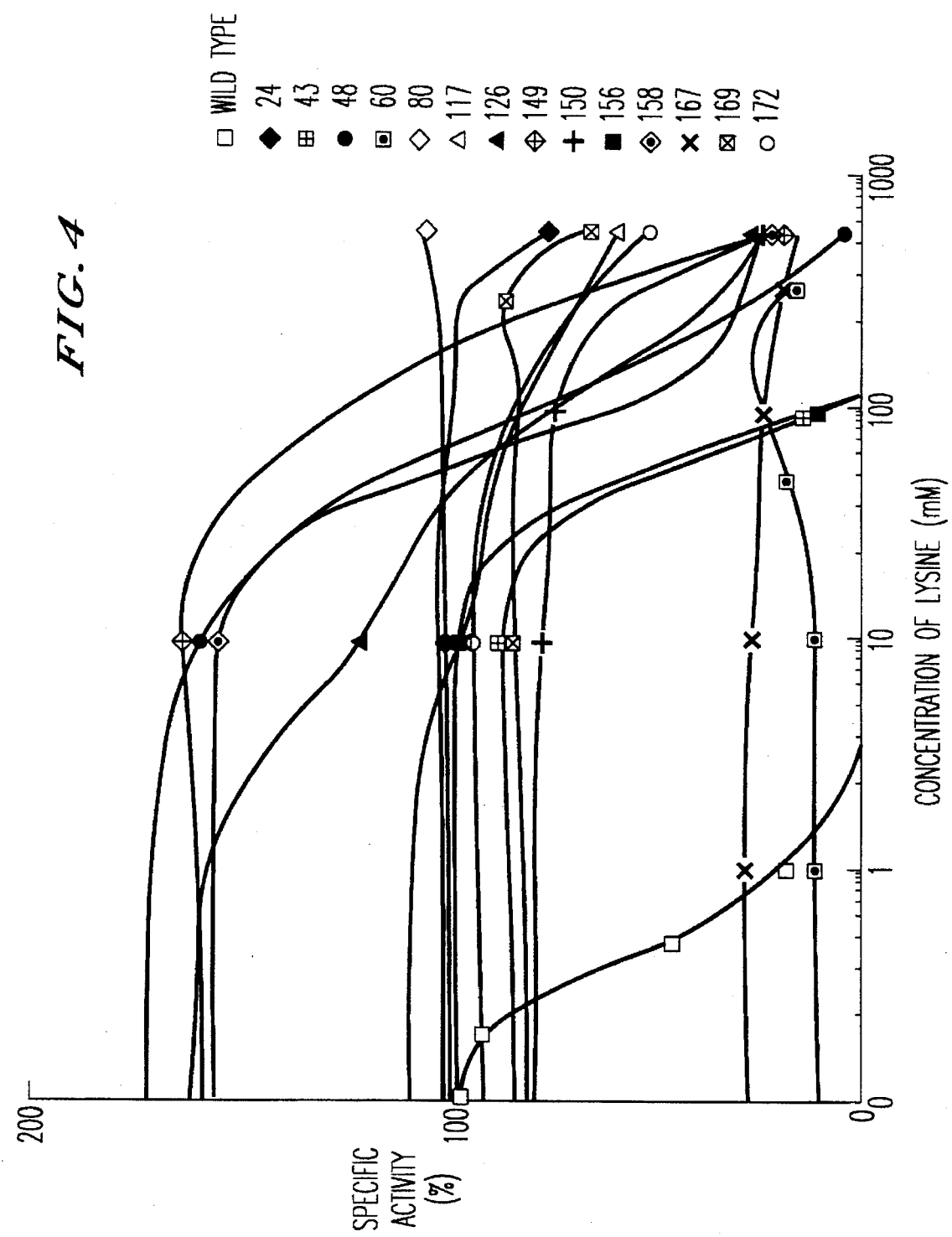
FIG. 4 shows the degree of lysine-dependent inhibition of aspartokinases coded for by various lysC* genes (See Example 3 (3-4)). The lysine concentrations on the horizontal axis are expressed as logarithms. The specific activities on the vertical axis are expressed as ratios defining as 100% the activity of a wild type of AK III with 0 mM addition of lysine.

The results are shown in FIG. 4.

(3-4); Degree of release of lysine-dependent inhibition

For the measurement of the enzyme activity of AK, lysine was added to the enzyme reaction solutions at various concentrations, and the levels of lysine-dependent inhibition were determined. The wild type of AK III was very strongly inhibited by lysine, e.g., with a 50% inhibition with about 0.45 mM of lysine, and roughly 100% inhibition with 5 mM thereof (FIG. 4).

In contrast, the mutants of AK III obtained here exhibited various degrees of release, but all 14 had some release of the lysine-dependent inhibition (FIG. 4, and Table 7). Particularly, in the case of Nos. 24, 80, 117, 169 and 172, practically no inhibition was observed even with 100 mM of lysine, and the 50% inhibition concentration was 200 fold or greater.

Also, the specific activity, the activity of the enzyme per unit protein, was equal to or greater than that of the wild type, even considering the influence of the growing conditions of the cells and the preparation of the sample, and there was seen no problem of reduced activity due to introduction of the mutations (Table 7). From this it was assumed that the active site of AK III and the site responsible for regulation by lysine are independent from each other.

In Table 7, the inhibition release is presented as the activity (%) in the presence of 100mM of lysine with respect to the activity of a lysine-free reaction solution, and the thermal stability is presented as the maintenance of activity (%) after treatment at 55° C. for 1.5 hours with respect to the activity without heating.

TABLE 7

| Inhibition release by lysine and thermal stability | | | |
|---|---|---|---|
| | Specific activity (μ/mg protein) | Inhibition release (%) | Thermal stability (%) |
| Wild type | 0.0247 | 0 | 18 |
| No. 117 | 0.0069 | 120 | 0 |
| No. 24 | 0.0218 | 100 | 30 |
| No. 80 | 0.0244 | 99 | 36 |
| No. 172 | 0.0189 | 97 | 0 |
| No. 169 | 0.0128 | 96 | 2 |
| No. 150 | 0.0062 | 77 | 25 |
| No. 126 | 0.0250 | 61 | 39 |
| No. 149 | 0.0256 | 59 | 9 |
| No. 167 | 0.0083 | 43 | 45 |
| No. 48 | 0.0228 | 38 | 42 |
| No. 60 | 0.0144 | 35 | 9 |
| No. 158 | 0.0224 | 22 | 42 |
| No. 156 | 0.0101 | 18 | 2 |
| No. 43 | 0.0212 | 17 | 0 |

(3-5); Thermal stability

When raising the level of activity of certain enzymes for their improvement, it is important that they be stably maintained within the cells. Because of the difference in the activity of proteases within and without the cells and the influence of the preservation buffer, measurement thereof is preferably made in vivo, but here for the sake of convenience, thermal stability as a parameter of each of the mutants of AK III was tested in vitro.

As a result of various tests regarding the temperature at which the inactivation of AK III occurs, the temperature was set to 56° C. and the rate of maintenance of activity was determined after the treatment effected for 90 minutes. As shown in Table 7 above, half of the mutants were superior to the wild type. In general, mutated proteins tend to be less stable than their wild types, but the some of the mutated types of AK III obtained here had a greater stability than the wild type, and many were thought to be very useful as enzymes for the practical production of L-threonine.

EXAMPLE 4

Fermentation production of L-threonine using a lys*C-introduced strain (4-1);

Of the heretofore known threonine-producing *E. coli* bacteria, the B-3996 strain exhibits the highest capability of threonine production. Here, it was decided to use the B-3996 strain as the host for the evaluation of lysC*. The B-3996 strain has been deposited at the Research Institute of Genetics and Selection of Industrial Microorganism under No. BKIIM (VKPM) B-3996. Furthermore, as the lysC* to be evaluated were provided 6 types with different degrees of inhibition release and specific activities (Nos. 24, 43, 60, 80, 149 and 167 in Table 7) for use in the following experiment.

Figure 5:
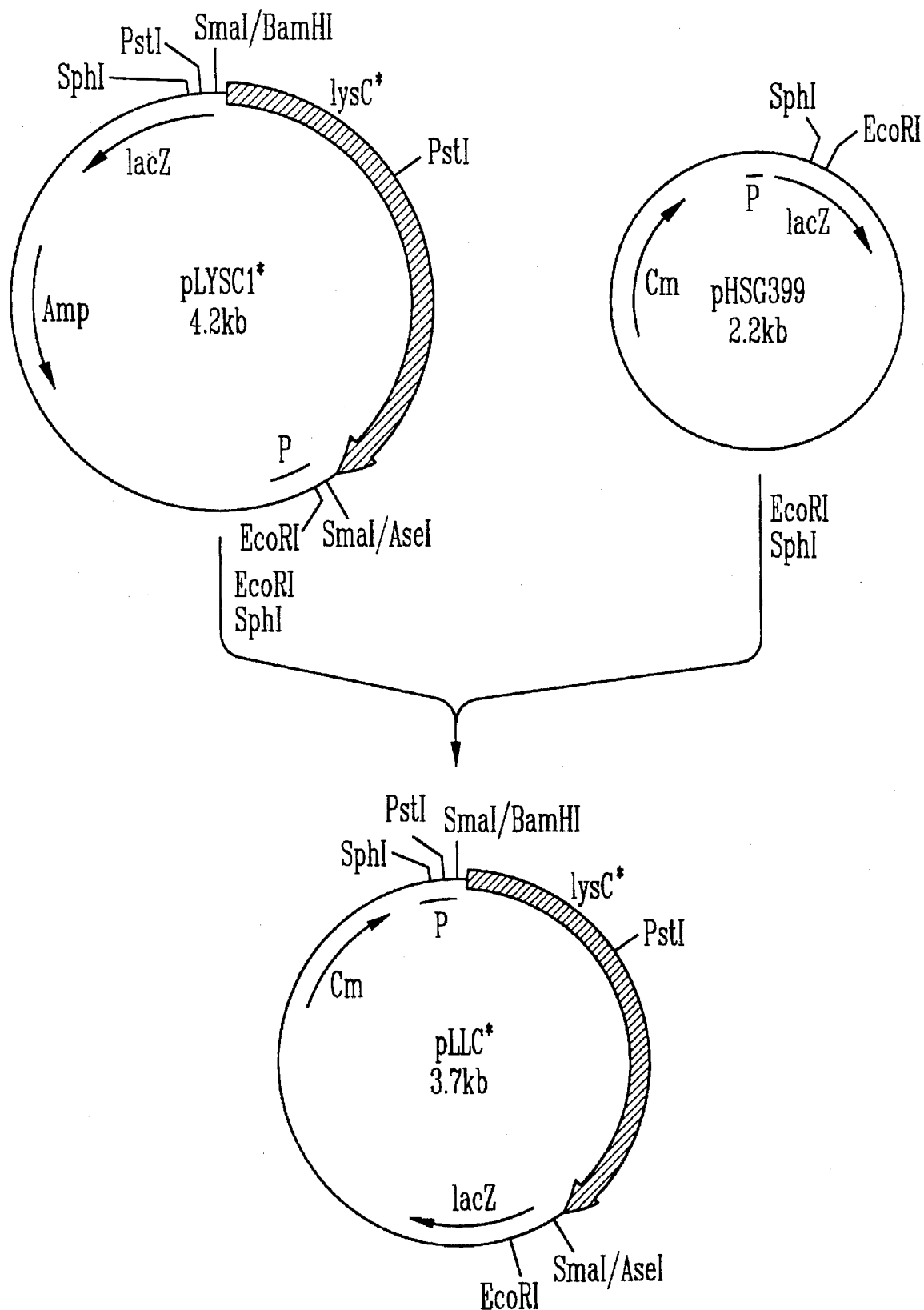
FIG. 5 shows a diagram for the construction of pLLC* (See Example 4 (4-1)).

First, in order to increase the degree of expression of the lysC*, each of the above mentioned 6 types of lysC* on pLYSC1* was transferred to the downstream of the lacZ promoter of the vector pHSg399 (product Of Takara Shuzo Co.) to effect the inverting insertion of each lysC*. The novel plasmids obtained in this manner were collectively named pLLC* series (FIG. 5). The *E. coli* HB101 strains into which the plasmids having the above lysC* Nos. 80 and 167 had been inserted were named AJ12750 and AJ12751, respectively, and they were originally deposited at the National Institute of Bioscience and Human Technology (Japan) as of Sep. 1, 1992. The AJ12750 was assigned No. FERM P-13136 (converted to an international deposit as of November 4, 1993 under No. FERM BP-4462), and the AJ12751 was assigned No. FERM 13137 (converted to an international deposit as of the same date under No. FERM BP-4463). The rest were not deposited, but since all of the mutation points for each lysC have been discovered, as described below, those having ordinary skill in the art may easily recover the plasmids from the above mentioned deposited bacteria following the method of Maniatis, et al. (Sambrook, J., Fritsch, E. F., Maniatis, T., Molecular CLoning, Cold Spring Harbor Laboratory Press, 1, 21, 1989), to obtain the object rest lysC* gene following the site directed mutagenesis method (Sambrook, J., Fritsch, E. F., Maniatis, T., Molecular Cloning, Cold Spring Harbor Laboratory Press, 15, 83, 1989). A conventional method was used to insert these plasmids into the B-3996 strain for evaluation.

The culturing was carried out using the following culture medium as shown in Table 8 below (the components A, B and C having been separately sterilized), for a culturing time of 38 hours, at a temperature of 37° C. with stirring at 114–116 rpm.

TABLE 8

Threonine production medium

| | | (g/l) |
|---|---|---|
| A: | $(NH_4)_2SO_4$ | 16 |
| | $KH_2PO_4$ | 1 |
| | $MgSO_4.7H_2O$ | 1 |
| | $FeSO_4.7H_2O$ | 0.01 |
| | $MnSO_4.5H_2O$ | 0.01 |
| | Yeast ext. (Difco) | 2 |
| | L-Met | 0.5 |

Adjusted to pH 7.0 with KOH, and autoclaved at 115° C. for 10 minutes (16/20 vol).

B: 20% glucose, autoclaved at 115° C. for 10 minutes (4/20 vol).

C: Pharmacopoeial $CaCO_3$, autoclaved at 180° C. for 2 days (30 g/l).

D: Antibiotics (100 μg/ml of streptomycin, and 5 μg/ml of kanamycin).

(4-2); Evaluation of lysC*

Each of the six pLLC* series plasmids was used for the transformation of the B-3996 strain, and each transformant was cultured under both conditions of addition of 1 g/l of lysine and no addition thereof, respecively. As controls, the host B-3996 strains with and without a plasmid possessing the wild type of lysC (pLLC1) were prepared.

The results are shown in Table 9 below. In the table, the values in the parentheses are the ratios of lysine yields (g) per 1 g consumed saccharide to the lysine yield (g) per 1 g consumed saccharide obtained when the B-3996 was cultured with no addition of lysine (control). This means that the latter yield is referred to as 1.00. The lysine sensitivity is defined as (lysine yield per consumed saccharide with addition of lysine)/(lysine yield per consumed saccharide with no addition of lysine). With respect to the B-3996 strain, the reduction in the yield per consumed saccharide observed in the lysine-added culture was approximately 0.74 on the basis of that observed in the non-added culture. However, in the case of the strains into which a lysC* had been introduced, for example, B-3996/pLLC*149, the reduction in the yield per consumed saccharide observed in the lysine-added culture was approximately 0.96 on the basis of that observed in the non-added culture. From this it is supposed that the AK III encoded by lysC contributes to the biosynthesis of threonine, and that the inhibition on AK III activity by the addition of lysine is, in turn, related to the inhibition on threonine biosynthesis. This phenomenon is diminished when the lysC* according to the present invention is used.

TABLE 9

| | Amount of Lys added (g/l) | Residual saccharide (g/l) | Thr (g/l) | Yield per consummed saccharide (%) | Lysine sensitivity |
|---|---|---|---|---|---|
| B-3996 | 0 | 0.09 | 12.1 | 30.7 (1.00) | |
| | 1 | 0.12 | 8.9 | 22.6 | 0.74 |
| B-3996/ pLLC1 (wild) | 0 | 0.07 | 13.1 | 33.0 (1.07) | |
| | 1 | 0.14 | 11.1 | 28.3 | 0.87 |
| B-3996/ pLLC*24 | 0 | 0.11 | 15.4 | 38.5 (1.25) | |
| | 1 | 0.08 | 12.7 | 32.3 | 0.84 |
| B-3996/ pLLC*43 | 0 | 0.09 | 15.1 | 38.3 (1.25) | |
| | 1 | 0.12 | 14.4 | 35.5 | 0.93 |
| B-3996/ pLLC*60 | 0 | 1.32 | 13.8 | 36.3 (1.18) | |
| | 1 | 2.66 | 11.6 | 31.4 | 0.86 |
| B-3996/ pLLC*80 | 0 | 0.10 | 15.7 | 39.7 (1.29) | |
| | 1 | 0.09 | 13.9 | 35.6 | 0.90 |
| B-3996/ pLLC*149 | 0 | 0.07 | 12.8 | 32.1 (1.04) | |
| | 1 | 1.80 | 11.3 | 30.7 | 0.96 |
| B-3996/ pLLC*167 | 0 | 0.07 | 15.5 | 39.8 (1.30) | |
| | 1 | 0.10 | 13.9 | 35.3 | 0.89 |

Also, regarding the threonine production of the lysine-free culture, it was clear that the strains which had the wild lysC plasmid gave improved productivity over the B-3996 strain having no such plasmids, and that the productivity was further increased by the strains having mutant lysC*s (approximately 1.3 times that of the host in case of No. 80). These results indicate that AK III is one of the rate-limiting factors in the production of threonine by the B-3996 strain. With the cells into which the mutant lysC* had been introduced, the lysine-free culturing gave an improved yield compared to that using the cells into which the wild lysC had been introduced, and it is thought that this was due to the fact that the latter exhibited inhibition on the wild type of AK III by lysine biosynthesized in the cells themselves.

(4-3); Stabilization of mutant lysC plasmids

Figure 6:
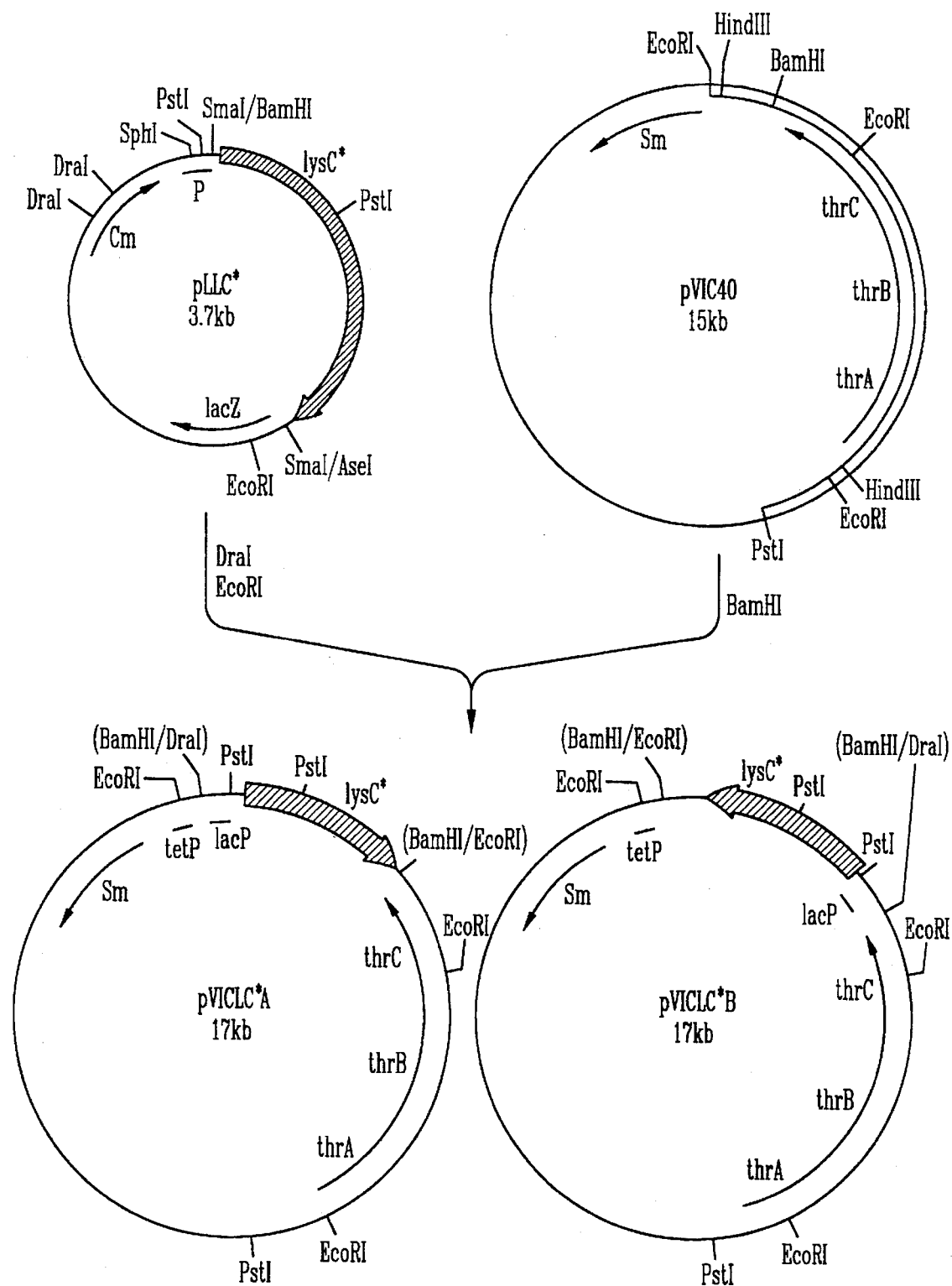
FIG. 6 shows a diagram for the construction of pVICLC*A and pVICLC*B (See Example 4 (4-3)).

Plasmids as shown in FIG. 6 were prepared with lysC* incorporated in both directions at the BamHI site of the plasmid pVIC40 extracted from the B-3996 strain. The method for collecting pVIC40 from the B-3996 strain was already described above. Selection was made of No. 80, which had a high level of threonine production, as the lysC* and of No. 43 for comparison therewith, to obtain 4 different plasmids, i.e., pVICLC*80A, pVICLC*80B, pVICLC*43A and pVICLC*43B.

For use as the host, B-399 strain (B-3996 strain with pVIC40 removed) was newly prepared by curing the B-3996 strain. The curing was achieved by repeating a 1/100-fold dilution three times with a streptomycin-free L-broth, with respect to a culture solution of the B-3996 strain. The culturing temperature here was 40° C. Into the B-399 strain obtained in this manner were introduced pVICLC*80A and pVICLC*43A, respectively, out of the 4 plasmids having lysC* incorporated therein, and culturing was effected. The results are shown in Table 10. The strains into which had been introduced pVICLC*80A or pVICLC*43A exhibited an increase in yield over the pVIC40 transformant strain (B-3996) being used as the control (1.10-fold with respect to pVICLC*80A, and 1.07-fold with respect to pVICLC*43A).

TABLE 10

| Plasmid | Residual saccharide (g/l) | Thr (g/l) | Yield per consumed saccharide (%) |
|---|---|---|---|
| pVIC40 | 0.15 | 14.0 | 35.7 (1.00) |
| pVICLC*43A | 0.09 | 14.9 | 38.0 (1.07) |
| pVICLC*80A | 0.09 | 15.3 | 39.1 (1.10) |
| pVIC40 + pLLC*43 | 0.97 | 15.8 | 41.1 (1.15) |
| pVIC40 + pLLC*80 | 6.15 | 13.7 | 41.3 (1.16) |

It is thought that the reduction in the degree of increase in the yields, compared with the results in (4-2), was due to a lower number of copies resulting from changing of the vector to pVIC40, but the growth was the same as for the B-3996 strain and the plasmids were stably maintained.

(4-4); Incorporation of mutant lysC* gene into chromosomes

The mutant type lysC* was introduced, utilizing the homologous recombination phenomenon, into the threonine-producing B-3996 by targeting the wild lysC gene on its chromosome. The method used here was a modification of the method of Russel et al. (Russel, M. and Model, P., J. Bacteriol., 159, 1034, 1984).

If the host is an *E. coli* mutant, i.e., the MM382 strain (polA$^{ts}$, available from the *E. coli* genetic stock center, U.S.A.), then the plasmid pHSG399 can replicate at 37° C. (permissive temperature), but not at high temperatures such as 42° C. (non-permissive temperature). This fact was utilized for the homologous recombination.

First, pLLC43* and pLLC80* were each introduced into the mutant strain MM383 as the host, at a temperature of 37° C. at which replication was possible, to obtain transformants MM383/pLLC* 43 and MM383/pLLC* 80, respectively. These transformants were cultured at 42° C., and selection was made of those which had lacked the plasmids but still remained resistant to chloramphenicol. The plasmids had been incorporated into the chromosomes of these strains. The obtained strains were named MM383-C43 and MM383-C80, respectively. These strains were infected with P1 phage, and a phage solution was prepared, which was used to infect the B-3996 strain. Selection was made of strains which had lysC* transducted into their chromosomes, using chloramphenicol resistance as the marker, and they were named B-3996-C43 and B-3996-C80, respectively.

Culturing of B-3996-C-43 and B-3996-C-80 was effected under the same conditions as in (4-1), and the results shown in Table 11 below were obtained. Approximately a 4% improvement in the yield of threonine production was observed.

TABLE 11

| | Amount of Lys added (g/l) | Thr (g/l) | Yield per consumed saccharide (%) |
|---|---|---|---|
| B-3996 | 0 | 14.1 | 34.8 (1.00) |
| | 1 | 9.9 | 24.6 |
| B-3996-C43 | 0 | 14.3 | 35.4 (1.02) |
| | 1 | 11.4 | 28.1 |
| B-3996-C80 | 0 | 14.6 | 36.1 (1.04) |
| | 1 | 11.2 | 27.7 |

EXAMPLE 5

Determination of base sequences of wild lysC and mutant lysC*

(5-1);

Using a DNA sequencer "ABI Model 373A" (ex ABI Co.), a conventional method was conducted to determine the base sequence of the wild lysC gene. The result is listed in the attached sequence listing under SEQ ID NO: 1. It was found that the sequence are different from the already published base sequence of lysC of *E. coli* K-12 JC411 (Cassan, M., Parsot, C., Cohen, G. N. and Patta, J. C., J. Biol. Chem., 261, 1052, 1986) in 6 bases (resulting in two amino acid residue changes). The 6 differences were thought attributable to the difference in the strains used.

(5-2); Base sequence of the feedback inhibition-resistant mutant lysC*

The base sequences of the 14 kinds of lysC* investigated in Example 3 were determined in the same manner as in (5-1), and the points of mutation were clearly found. The results are shown in Table 12. Of the 14 kinds, two exactly identical pairs were present, and thus there were 12 kinds of actual mutants. Mutant Nos. 149, 150, 156, 158, 167, 169 and 172 had been obtained by treatment with hydroxylamine and Nos. 24, 43, 48, 60, 80, 117 and 126 by treatment with NTG. However, the patterns of mutation were all C→T or G→A; the mutation of G→A had been given through the mutation of C→T on the complimentary strand.

TABLE 12

Identification of Mutation Points of lysC*

| Mutant types lysC* | Mutagen (a) | Mutation point (amino acid change) |
|---|---|---|
| No. 126 | N | GGT→GA*T ($^{323}$Gly→Asp) |
| No. 43 | N | GGT→GA*T ($^{323}$Gly→Asp) |
| | | GGC→GA*C ($^{408}$Gly→Asp) |
| No. 149 | H | CGT→T*GT ($^{34}$Arg→Cys) |
| | | GGT→GA*T ($^{323}$Gly→Asp) |
| No. 43/167 | N/H | CTC→T*TC ($^{325}$Leu→Phe) |
| NO. 150 | H | ATG→ATA* ($^{318}$Met→Ile) |
| No. 172 | H | $^{775}$C→T (silent) |
| | | ATG→ATA ($^{318}$Met→Ile) |
| | | GTG→A*TG ($^{349}$Val→Met) |
| No. 117 | N | TCA→TT*A ($^{345}$Ser→Leu) |
| No. 158 | H | GTG→A*TG ($^{347}$Val→Met) |
| No. 24/80 | N/N | ACC→AT*C ($^{352}$Thr→Ile) |
| No. 169 | H | $^{923}$C→T (silent) |
| | | ACC→AT*C ($^{352}$Thr→Ile |
| | | TCT→TT*T ($^{369}$Ser→Phe) |
| No. 60 | N | $^{859}$G→A (silent) |
| | | GAA→A*AA ($^{164}$Glu→Lys) |
| No. 156 | H | ATG→ATA* ($^{417}$Met→Ile) |
| | | TGT→TA*T ($^{419}$Cys→Tyr) |
| | | $^{2014}$C→T (silent) |

(a) H: hydroxylamine treatment, N: NTG treatment (5-3); Identification of domains contributing to release of feedback inhibition A large number of mutations were present at the C-end, and they were particularly concentrated at the A domain (from the 318th Met residue to the 325th Leu residue) and the B domain (from the 345th Ser residue to the 352nd Thr residue) of FIG. 7 (see "Mutation points" column in Table 12). E. coli has two types of AK, thrA (AK I-HD I) and metL(M) (AK II-HD II), in addition to lysC (AK III). The mutant lysC* had two locations having a high degree of homology to the two types, and these domains are thought to be the active center of AK (Cassan, M., Parsot, C., Cohen, G. N. and Patte, J. C., J. BIol. Chem., 261, 1052, 1986). The A and B domains at the C-end are outside of these common domains, and thus it is highly possible that they are lysine-controlled domains specific to AK III. Particularly, Nos. 24/80, 172, 169 and 117 with a high degree of inhibition release had mutations in the B domain, which fact is thought to be important. Of the 12 types, 10 had mutations in either the A or B domain. Nos. 60 and 158 were exceptional, and showed low levels of both release of inhibition and thermal stability (Table 7 above), and this is thought to be a result of partial release of the inhibition due to a change in the structure of the enzyme as a whole by mutation. Also, in the case of the mutant types having multiple mutation points, there is the question of which mutation point is effective, and the following explanation may be given based on comparison with the mutant types having a single mutation at the same site.

(1) Nos. 126 (1 point), 43 (2 points) and 149 (2 points)

The mutation point of No. 126 in the A domain is common to all the three mutant types, while the degree of inhibition release is the same for Nos. 149 and 126, and the greater number of mutation points in No. 43 resulted in rather opposite effect. This leads to the assumption that the mutation point of No. 126 in the A domain is the one which imparts the inhibition release.

(2) Nos. 24/80 (1 lpoint) and 169 (2 points)

Of the two mutation points in No. 169, the one in the B domain was the same as that in No. 24/80. Both produced a 100% degree of inhibition release, and therefore the mutation point in No. 24/80 is sufficient.

(3) Nos. 150 (1 point) and 172 (2 points)

No. 150 has one mutation point in the A domain, while No. 172 has two mutations each in the A domain (same as No. 150) and the B domain, respectively. The degree of inhibition release was stronger with No. 172, making it clear that both the A domain and the B domain contribute to the inhibition release.

In the manner described above, the present inventors have identified the domain relating to the release of the lysine-dependent inhibition of aspartokinase activity in the A domain (when expressed in terms of amino acid residues, from the 318th Met residue to the 325th Leu residue) and the B domain (from the 345th Ser residue to the 352nd Thr residue). However, the present inventors have not concluded that the release of the lysine-dependent inhibition of aspartokinase activity occurs only in the case of mutation wherein some specific amino acid residues are changed to some other amino acid residues. For example, in Table 12 it is shown that release of the feedback inhibition occurs when the 323rd glycine residue is changed to an aspartic acid residue, but it is clear to a person having ordinary skill in the art that the same release occurs even when it is replaced by a glutamic acid residue instead of an aspartic acid residue. This is because plural amino acids which have a similar structure, such as aspartic acid and glutamic acid, are called homologous amino acids, and exchange of an amino acid for its homologous one is not considered to cause any great change in the function of the protein (A list of homologous amino acids is found in Protein Engineering, p.31, CMC Co., 1985).

It is often observed that exchange of an amino acid for a non-homologous amino acid has the same effect as that for a homologous one. Conversely, exchange of an amino acid for a homologous amino acid sometimes produces dramatic changes in the function of the protein (Estell, D. A., Graycar, T. P., and Wells, J. A., J. Biol. Chem., 260, 6518, 1988; Schultz, S. C., and Richards, J. H., Procedure. Natl. Acad. Sci. USA, 83, 1588, 1986; Yutani, K., et al., J. Biol. Chem., 262, 13429, 1987; Yutani, K., et al., Procedure. Natl. Acad. Sci. USA, 84, 4441, 1987; Nishiyama, M., et al., J. Biol. Chem., 266, 14294, 1991).

Furthermore, according to the present invention, some of the amino acid residues in the A and B domains were not changed, but since the functions Of the proteins are defined on the basis of domain units, it is reasonable to assume that release of feedback inhibition will be observed by introducing one or more amino acid residue mutations in the domains which have not been introduced this time. In fact, a number of such examples have been reported (Furuya, H., et al., Biochemistry, 28, 6848, 1989; Furuya, H., et al. Biochem. Biophys. Research. Commun., 160, 669, 1989; Cunningham, B. C. and Wells, J. A., Science, 244, 1081, 1989).

In short, the present invention is characteristically based on the present inventor's discovery of the domains relating to the feedback inhibition. In the Examples, only a few patterns of mutation in the domains are disclosed, but as described above, it is clear to a person having ordinary skill in the art that other patterns of mutation may produce the same effect. Therefore, such mutations are also within the scope of the present invention.

Industrial Applicability

As mentioned above, Escherichia bacteria-derived AK III genes have been obtained which sufficiently release the feedback inhibition due to lysine. By introducing these genes into threonine-producing bacteria, it is possible to obtain other threonine-producing bacteria which were much improved in threonine production over those of the prior art. The successful use of these threonine-producing bacteria has provided a much more excellent method for the production of L-threonine by fermentation than the conventional methods.

What is claimed is:

1. A DNA encoding aspartokinase III having a mutated amino acid sequence in which the amino acid sequence of SEQ ID NO:1 has a mutation selected from the group consisting of i) replacement of Gly 323 by Asp;

ii) replacements of Gly 323 by Asp and Gly 408 by Asp;

iii) replacements of Arg 34 by Cys and Gly 323 by Asp;

iv) replacement of Leu 325 by Phe;

v) replacements of Met 318 by Ile and Val 349 by Met;

vi) replacement of Ser 345 by Leu;

vii) replacement of Val 347 by Met;

viii) replacements of Thr 352 by Ile and Ser 369 by Phe;

ix) replacement of Glu 164 by Lys; and x) replacements of Met 417 by Ile and Cys 419 by Tyr.

2. A recombinant DNA wherein the DNA of claim 1 is linked to a vector DNA capable of autonomous replication in an Escherichia bacterial cell.

3. A microorganism belonging to the genus Escherichia which has been transformed by the introduction into its cell of the recombinant DNA according to claim 2.

4. A method for the production of L-threonine which comprises culturing a microorganism according to claim 3 in a fermentation medium, whereby L-threonine is produced and accumulated in the culture medium, and collecting the L-threonine from said culture medium.

5. A DNA encoding aspartokinase III having a mutated amino acid sequence in which the amino acid sequence of SEQ ID NO:1 has a mutation selected from the group consisting of:

i') replacement of Met 318 by Ile; and ii') replacement of Thr 352 by Ile.

6. A recombinant DNA wherein the DNA of claim 5 is linked to a vector DNA capable of autonomous replication in an Escherichia bacterial cell.

7. A microorganism belonging to the genus Escherichia which has bene transformed by the introduction into its cell of the recombinant DNA according to claim 6.

8. A method for the production of L-threonine which comprises culturing a microorganism according to claim 7 in a fermentation medium, whereby L-threonine is produced and accumulated in the culture medium, and collecting the L-threonine from said culture medium.

* * * * *